United States Patent
Maggiore

(10) Patent No.: US 10,029,425 B2
(45) Date of Patent: Jul. 24, 2018

(54) CONTAINER FOR ACCOMMODATING AT LEAST ONE OF AT LEAST ONE BIOLOGICALLY ACTIVE FLUID AND AT LEAST ONE PREPARATORY FLUID, AND A METHOD THEREFOR

(71) Applicant: Sartorius Stedim Biotech GmbH, Goettingen (DE)

(72) Inventor: Frank Maggiore, Port Jefferson Station, NY (US)

(73) Assignee: Sartorius Stedim Biotech GmbH (DE)

( * ) Notice: Subject to any disclaimer, the term of this patent is extended or adjusted under 35 U.S.C. 154(b) by 660 days.

(21) Appl. No.: 14/680,180

(22) Filed: Apr. 7, 2015

(65) Prior Publication Data
US 2016/0297152 A1    Oct. 13, 2016

(51) Int. Cl.
| | |
|---|---|
| *B29C 67/00* | (2017.01) |
| *B33Y 10/00* | (2015.01) |
| *B33Y 30/00* | (2015.01) |
| *B33Y 99/00* | (2015.01) |
| *B29C 64/106* | (2017.01) |
| *B29C 64/20* | (2017.01) |
| *B29C 64/35* | (2017.01) |
| *B29C 64/314* | (2017.01) |
| *B29C 64/227* | (2017.01) |

(Continued)

(52) U.S. Cl.
CPC ........ *B29C 67/0096* (2013.01); *B29C 64/106* (2017.08); *B29C 64/20* (2017.08); *B29C 64/35* (2017.08); *B33Y 10/00* (2014.12); *B33Y 30/00* (2014.12); *B33Y 99/00* (2014.12); *A61L 2/00* (2013.01); *B29C 64/209* (2017.08); *B29C 64/227* (2017.08); *B29C 64/241* (2017.08); *B29C 64/25* (2017.08); *B29C 64/255* (2017.08); *B29C 64/307* (2017.08); *B29C 64/314* (2017.08); *B29C 64/364* (2017.08); *B29L 2031/753* (2013.01); *B33Y 40/00* (2014.12)

(58) Field of Classification Search
CPC ............ B29C 67/0051; B29C 67/0055; B29C 67/0081; B29C 67/0085; B29C 67/0096; B29C 2791/005; B29C 64/209; B29C 64/227; B29C 64/241; B29C 64/25; B29C 64/255; B29C 64/307; B29C 64/314; B29C 64/364
USPC .... 425/375, 210, 174.4, 185, 112, 553, 289; 264/308, 39, 241, 113
See application file for complete search history.

(56) References Cited

U.S. PATENT DOCUMENTS

| | | | |
|---|---|---|---|
| 2005/0061241 A1* | 3/2005 | West | A61L 2/10 118/620 |
| 2015/0217514 A1* | 8/2015 | Maier | B29C 67/0059 264/241 |
| 2017/0021565 A1* | 1/2017 | Deaville | B29C 70/382 |

* cited by examiner

Primary Examiner — Matthew J Daniels
Assistant Examiner — Lawrence D. Hohenbrink, Jr.
(74) Attorney, Agent, or Firm — Gerald E. Hespos; Michael J. Porco; Matthew T. Hespos

(57) ABSTRACT

A sterilizable container for accommodating at least one of at least one biologically active fluid and at least one preparatory fluid has an area within the container configured to accommodate at least one sterilizable three-dimensional printer assembly. The sterilizable three-dimensional printer assembly includes at least one printing platform; at least one printer head for dispensing structural material onto the at least one printing platform to form thereon a three-dimensional structure; and a moving mechanism for providing a relative displacement between the at least one printer head and the at least one printing platform. The area is configured so that the fluid can reach the printer assembly.

12 Claims, 9 Drawing Sheets

(51) Int. Cl.
*B29C 64/307* (2017.01)
*B29C 64/209* (2017.01)
*B29C 64/255* (2017.01)
*B29C 64/25* (2017.01)
*B29C 64/241* (2017.01)
*B29C 64/364* (2017.01)
*B29L 31/00* (2006.01)
*A61L 2/00* (2006.01)
*B33Y 40/00* (2015.01)

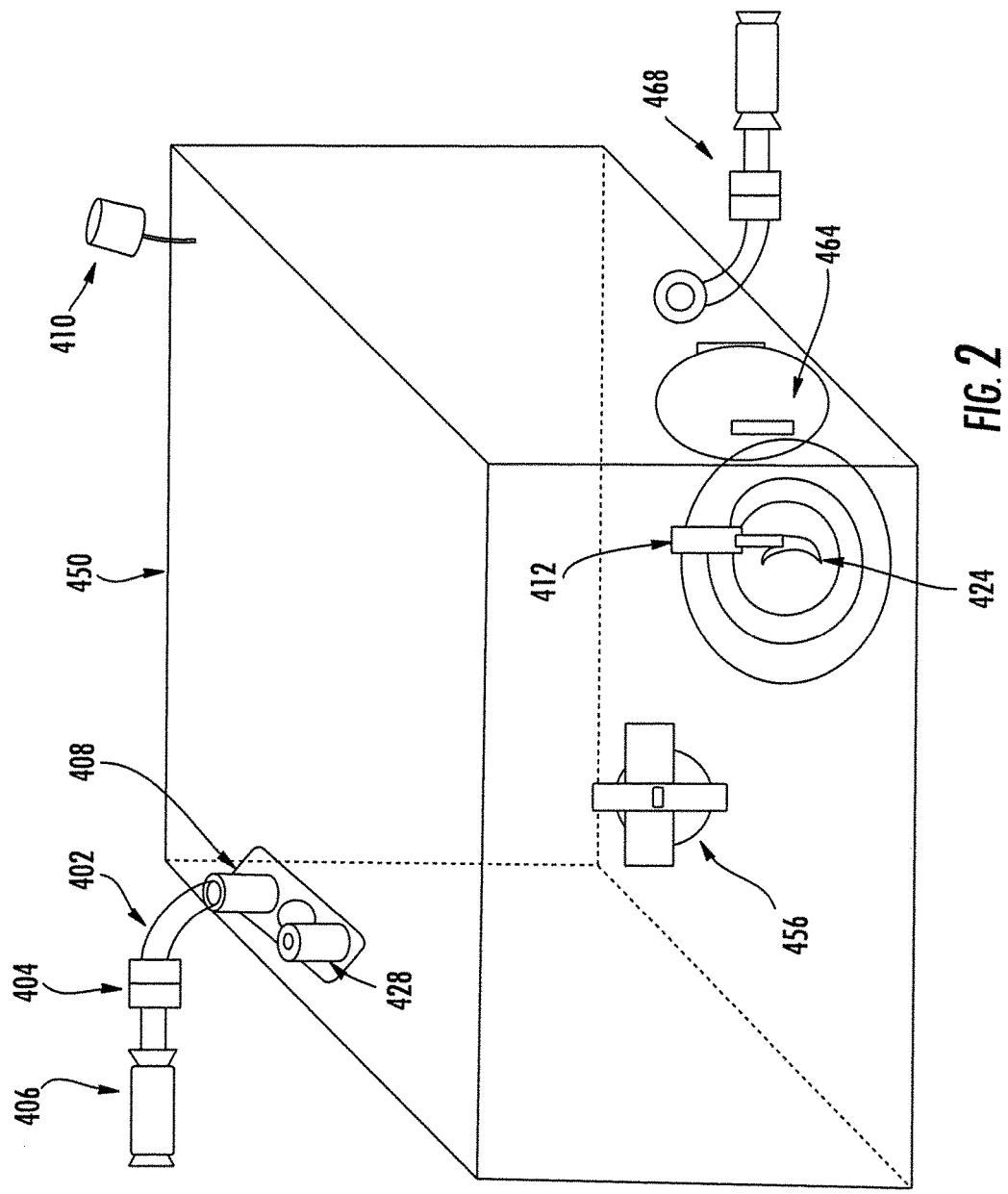

CONTAINER FOR ACCOMMODATING AT LEAST ONE OF AT LEAST ONE BIOLOGICALLY ACTIVE FLUID AND AT LEAST ONE PREPARATORY FLUID, AND A METHOD THEREFOR

BACKGROUND

1. Field of the Invention

The present invention relates to a container for accommodating at least one of at least one biologically active fluid and at least one preparatory fluid, like e.g. a bioreactor or a mixing container, which comprises an area for accommodating a three dimensional printer assembly, and a method of forming a three-dimensional structure in the container for accommodating at least one of the biologically active fluid and the preparatory fluid.

2. Description of the Related Art

Three-dimensional printers are intended to print out three-dimensional structures onto a printing platform. After the structure is formed, the printed components can be immersed in media during a cell/culture fermentation process or for preparing the three-dimensional printed objects for further processing. The respective media may be contained e.g. in a bioreactor or a mixing container. Currently, a three-dimensional structure can be printed in a three-dimensional printer and is afterwards transferred to a separate bioreactor or mixing container for further processing. However, when transferring the three-dimensional structure from the three-dimensional printer towards e.g. a bioreactor, the problem arises in the prior art that the sterile conditions for the three-dimensional structure have to be maintained during the transfer. This problem has been solved in the prior art by spending an extensive technical effort.

Accordingly, the present invention is intended to solve the problem of forming three-dimensional structures and providing them for further processing under sterile conditions in a simplified manner.

SUMMARY OF THE INVENTION

This technical problem has been solved by a sterilizable container for accommodating at least one of at least one biologically active fluid and at least one preparatory fluid, comprising:
an area within the container configured to accommodate at least one sterilizable three-dimensional printer assembly;
a sterilizable three-dimensional printer assembly including:
at least one printing platform;
at least one printer head for dispensing structural material onto the at least one printing platform in order to form thereon a three-dimensional structure; and
a moving mechanism for providing a relative displacement between the at least one printer head and the at least one printing platform,
wherein the area is configured such that the fluid can reach the printer assembly.

The term "sterilizable" is understood to mean that the container is suitable to be sterilized in order to provide aseptic conditions especially within the container, so that any biological and/or chemical processes in the container carried out by the at least one biologically active fluid and/or preparatory fluid are not influenced. Exemplary sterilizable containers are made of glass, stainless steel or plastic. The sterilization may be carried out by e.g. gamma-irradiation, autoclaving, steam-in-place, and/or chemical sterilant (such as ethylene oxide or vaporized hydrogen peroxide).

The same applies for the "sterilizable three-dimensional printer assembly" respectively. In particular, the three-dimensional printer assembly is suitable to be sterilized in order to provide aseptic conditions in the printer assembly. The components of the printer assembly are, therefore, adapted to be sterilizable. For example, the components of the printer assembly are made of metal, plastic and/or glass.

The "structural material", which is dispensed onto the at least one printing platform may form a matrix, a scaffolding, and/or a support including but not limited to polylactic acid (PLA), acrylonitrile butadiene styrene (ABS), carbon fiber, metal, hydroxyapatite (HA), collagen, fibrin, hydrogels, chitosan, hyaluronic acid, or other structural materials.

The three-dimensional structure printed by the three-dimensional printer assembly may have any shape depending on the desired product, which shall be produced afterwards by using the three-dimensional structure. In particular, cell cultures may be seeded onto the three-dimensional structure in order to grow at the three-dimensional product. For example, live cells, cell component products, such as proteins, antibodies, lipids, byproducts of the cell/culture fermentation process, such as alcohols or waste products, or recombinant expressed proteins, may be uniformly and/or selectively seeded and/or actively dispensed onto the three-dimensional structure The at least one biologically active fluid preferably comprises those cell cultures so that the cell cultures are seeded onto the three-dimensional structure as soon as the biologically active fluid contacts the three-dimensional structure.

If the printer assembly is contained in a container for accommodating at least one biologically active fluid, the biologically active fluid can be guided to the three-dimensional structure after its printing process. If the printer assembly is contained in a container for accommodating at least one preparatory fluid, the three-dimensional structure may be prepared by the at least one preparatory fluid before the cell cultures are seeded onto the three-dimensional structure. After the preparation process, the biologically active fluid may be pumped into the container for accommodating at least one preparatory fluid so that the cell cultures can seed onto the three-dimensional structure in the same container, or the prepared three-dimensional structure is transferred to a container for accommodating at least one biologically active fluid in a sterile manner by e.g. a transfer hatch.

In one example, the biological active fluid is dispensed by the at least one printer head onto the three-dimensional structure. The biological active fluid can be dispensed from a homogeneous or heterogeneous source. Multiple biological active materials can be dispensed by a plurality of printer heads or by a single printer head. Preferably, the printer head provides a flush step when switching between biological active materials. The biological active materials can additionally comprise nutrient rich materials such as sugar, serum, or other materials to provide a nutrient resource to encourage cell growth, adhesion of one or more cell types onto the printed three-dimensional structure.

The three-dimensional product which is grown on the three-dimensional structure printed by the printer assembly may include 3D printed functional tissue for in vitro efficacy and/or toxicology testing of pharmaceuticals; biosensors which are used for the detection of an analyte, by combining a biological component with a physiochemical detector (electrochemical, optical, thermal and/or piezoelectric); diagnostic membranes where a membrane is seeded with cells or cell products for the purposes of in vitro diagnostics or environmental analysis; cellular tissues for replacement therapies such as skin, muscle, neurons, and other tissues; scaffolding structures such as bone, cartilage, ligaments, and other biological structural materials, engineered tissue products such as replacement blood vessels, tendons, biologically derived stents, peripheral vascular devices, and other engineered products; engineered products combining tissues with electronic components such as seeding an implantable electronic device with cells to reduce incompatibility upon implantation and/or provide increased functionality of the tissue/organ; partially and/or fully functional organs such as livers, kidneys, hearts, lungs, reproductive organs, spinal cords, brain tissue, and other replacement organs; decellularization of an organ or biological component to remove all of the cells while maintaining the complete structure and recellularization of the remaining structure to return it to a functional organ; regenerative medical products such as utilizing patient derived cells within the 3D printed product to limit and/or prevent patient rejection due to incompatibility with the immune system.

The present invention provides the advantage that the three-dimensional structure is printed directly in the container for accommodating at least one biologically active fluid (i.e., liquid and/or gas) and/or at least one preparatory fluid (i.e. liquid and/or gas). It is no longer required to provide a separate external three-dimensional printer assembly from which the printed three-dimensional structure has to be removed and transferred afterwards to the container for accommodating a biologically active fluid and/or preparatory fluid. In particular, the three-dimensional structure can remain in the sterilized environment of the container for accommodating a biologically active fluid and/or preparatory fluid. Thereby, the technical effort for transferring the three-dimensional structure from an external three-dimensional printer assembly to a container for accommodating a biologically active fluid and/or preparatory fluid can be prevented. In other words, the three-dimensional structure is printed in the container for accommodating a biologically active fluid and/or preparatory fluid, whereby the biologically active fluid and/or preparatory fluid, or a part of this, are used to be seeded onto the three-dimensional structure and/or to prepare the three-dimensional structure for further processing.

Preferably, the printer assembly comprises a printer assembly housing which encloses at least partly the printer assembly in a sterile manner.

The printer assembly housing provides the possibility of accommodating the biologically active fluid and/or preparatory fluid in the container for accommodating the biologically active fluid and/or preparatory fluid while the printer assembly prints the three-dimensional structure. The biologically active fluid and/or preparatory fluid, however, can be prevented from entering the printer assembly housing during the printing process.

Preferably, the moving mechanism comprises at least one curved arm, which is supported by a supporting surface arranged adjacent to the at least one printing platform, wherein at least one printer head is attached to the curved arm.

The term "adjacent" is understood to mean that the supporting surface is arranged next to the supporting surface such that the at least one printer head attached to the curved arm is able to dispense structural material onto the at least one printing platform. "Adjacent" thereby means also that the supporting surface may be arranged at a level below or above the level of the at least one printing platform.

A curved arm as a supporting structure for holding at least one printer head allows a space saving supporting structure, which does not limit the space for printing a three-dimensional structure. Moreover, the curved arm does not obstruct the access to the finally printed three-dimensional structure for the user when removing the three-dimensional structure from the container for accommodating a biologically active fluid and/or preparatory fluid.

Preferably, the curved arm is movable between a retracted position and an extended position with respect to the supporting surface.

In other words, the curved arm is movable between the end positions "retracted position" and "extended position". However, this does not mean that the curved arm can only be arranged in the latter mentioned positions. The curved arm can also rest in any positions between the retracted position and the extended position.

Thereby, the at least one printer head, which is attached to the curved arm, is movable towards the desired positions in order to dispense structural material and/or the biologically active fluid onto the at least one dispensing platform and/or the three-dimensional structure at desired positions. Moreover, the three-dimensional structure formed by the printer assembly can be removed from the container for accommodating a biologically active fluid and/or preparatory fluid in a simplified manner after the curved arm has been shifted towards the retracted position.

Preferably, the curved arm extends through a through hole in the supporting surface.

The through hole allows the movement of the curved arm between the retracted position and the extended position. When extending through the through hole in the supporting surface, a portion of the curved arm projects from the supporting surface towards an upper side of the printer assembly, while another portion of the curved arm projects from the supporting surface towards an underside of the printer assembly. At the portion of the curved arm projecting towards the upper side of the printer assembly the at least one printer head is arranged. Depending on the state of the curved arm, the ratio of the portion of the curved arm projecting towards the upper side with respect to the portion of the curved arm projecting towards the underside varies. If the curved arm is arranged in the retracted state, the portion of the curved arm projecting towards the underside is larger than the portion of the curved arm projecting towards the upper side. The same applies vice versa for the extended position.

Preferably, the at least one printer head is at least one of movable along the curved arm and pivotable with respect to the curved arm.

Thereby a higher degree of freedom for the printer head is achieved, so that the three-dimensional structure can be printed in an improved manner.

Preferably, the printer head has at least one dispenser for dispensing the structural material onto the at least one printing platform, wherein the dispenser is fixed or movable with respect to the printer head.

If the dispenser is movable, the dispenser may be movable in multiple axis and dimensions to precisely dispense the structural and/or biological active materials.

Preferably, the supporting surface is movable or stationary.

In case the supporting surface is stationary, more than one curved arm may be provided which are arranged around the at least one printing platform, in order to be able to dispense structural material and/or biological material onto the printing platform and/or the three-dimensional structure from different sides. The supporting surface may be also divided into a plurality of supporting surfaces, wherein at least one curved arm is supported by a respective supporting surface.

In case the supporting surface is movable, the supporting surface together with the at least one curved arm, which is supported by the supporting surface, may be moved around the at least one printing platform. Additionally or alternatively, the supporting surface may be movable such that the distance towards the at least one printing platform can be changed. This can be achieved by changing the distance along the same level of the at least one printing platform or by changing the distance along the height direction. If the supporting surface is movable, the amount of required curved arms can be reduced, in order to print a three-dimensional structure.

In case more than one supporting surface is provided, the individual supporting surfaces may be stationary or movable.

Preferably, a driving assembly is arranged at an underside of the printer assembly for actuating at least one of the at least one curved arm and the at least one printing platform and the supporting surface, wherein the underside of the printer assembly is sealed with respect to an upper side of the printer assembly where the three-dimensional structure is formed.

The driving assembly is a sensible component of the printer assembly, which should not come in contact with any one of the biologically active fluids and/or the preparatory fluids, as components of the driving assembly, like e.g. motor(s), gears, sensor(s), load cell(s), could be damaged by the fluids and as materials used for the driving assembly, like e.g. oil, should not be mixed with the biologically active fluids and/or preparatory fluids. By arranging the driving assembly at the underside of the printer assembly, which is sealed with respect to the upper side of the printer assembly, the driving assembly can be protected from any contact with the biologically active fluids and/or preparatory fluids. After the three-dimensional structure has been printed, the biologically active fluids and/or the preparatory fluids will only be present at the upper side of the printer assembly, when e.g. seeding cell cultures onto the three-dimensional structure and/or preparing the three-dimensional structure for further processing. However, the biologically active fluids and/or preparatory fluids are prevented from entering the underside of the printer assembly by sealing elements, which are arranged preferably between any edges of the components of the printer assembly, where the access of the biologically active fluids and/or preparatory fluids to the underside of the printer assembly has to be prevented.

Preferably, a feed assembly is arranged at the underside of the printer assembly, which is connected to the at least one printer head via at least one conduit extending through the at least one curved arm for feeding the at least one printer head with the structural material.

The feed assembly is also a sensible component of the printer assembly, which should not come in contact with any one of the biologically active fluids and/or preparatory fluids, as the feed assembly could be damaged by the fluids and as materials used for the feed assembly should not be mixed with the biologically active fluids and/or preparatory fluids. After the three-dimensional structure has been printed, the biologically active fluids and/or preparatory fluids will only be present at the upper side of the printer assembly, when e.g. seeding cell cultures onto the three-dimensional structure and/or preparing the three-dimensional structure for further processing. However, the biologically active fluids and/or preparatory fluids are prevented from entering the underside of the printer assembly by sealing elements.

The feed assembly may e.g. comprise a pump for pumping the structural material and/or biological active fluid to the printer head and/or a heating element for heating the structural material and/or the biologically active fluid to a desired temperature, which provides an advantageous dispensing temperature. By means of at least one conduit, which extends through the at least one curved arm and which is adapted to conduct the structural material and/or the biologically active fluid from the underside of the printer assembly to the at least one printer head at the upper side of the printer assembly, the structural material and/or the biological active fluid can be pumped from the underside to the upper side of the printer assembly in a safe manner. In particular, the at least one conduit is not exposed to the biologically active fluid and/or the preparatory fluid and the need of one or more further through holes through e.g. the supporting surface(s) through which the at least one conduit extends from the under side to the upper side of the printer assembly can be prevented. Thereby, the effort for sealing the upper side from the underside of the printer assembly can be reduced.

The upper side of the printer assembly can be a limited area in the container defined by a single-use assembly. By means of an attachment mechanism, like e.g. a snap mechanism, the single use assembly may be connected with the feed assembly and/or driving assembly. The feed assembly and/or the driving assembly may be a single-use or multiple-use assembly.

Preferably, the printer assembly housing comprises at least one of at least one controlled fluid inlet port and at least one controlled fluid outlet port for allowing a fluid exchange between the printer assembly housing and the container.

During the printing process, the printer assembly housing is sealed with respect to the container for accommodating at least one biologically active fluid and/or preparatory fluid, so that the biologically active fluid and/or the preparatory fluid is only present in the container for accommodating a biologically active fluid and/or preparatory fluid. After the printing process, the at least one controlled fluid inlet port is openable, so that the biologically active fluid and/or the preparatory fluid contained in the container for accommodating biologically active fluid and/or preparatory fluid is enabled to flow into the printer assembly housing for filling the chamber at the upper side of the printer assembly where the printed three-dimensional structure is present. The at least one fluid outlet port is also openable to allow air to vent out and allow the chamber to be completely filled with fluid from the container for accommodating a biologically fluid and/or preparatory fluid. However, the at least one fluid outlet port may be configured such that fluid and/or gas may be prevented from entering into the printer assembly housing but allows air/gas to exhaust out of the printer assembly housing. The process of filling and removing fluid from the printer assembly housing can occur a plurality of times according to the required processing. This can support the layering of multiple materials and/or the layering of different cell types onto the three-dimensional structure. Adhesion promoting materials can be sprayed onto the three-dimensional structure at the conclusion of each fluid removal step to promote the next layer of cells to adhere to the surface.

In consequence, there is no need to open the container for accommodating a biologically fluid and/or preparatory fluid or the printer assembly housing between the printing process and the seeding or preparation process so that the sterile conditions inside of the container and housing can be maintained in a reliable manner.

Preferably, the printer assembly housing is openable.

In particular, the printer assembly housing may comprise a hood or a lid, which is openable to provide the user access to the printed three-dimensional structure after the printing process and/or after the seeding or preparation process as described above.

Preferably, the container is one of a bioreactor and a mixing container.

In the bioreactor, various biologically active fluids are contained for cell growth or fermentation. For providing the perfect conditions for the cell growth and/or fermentation, the bioreactor may be equipped with various sensors which measure different relevant parameters of the biologically active fluids and a control unit which analyses the measured parameters and adjusts the parameters if required. Possible parameters are temperature or oxygen content, etc. The bioreactor may be formed as a rigid or a flexible container. Particularly, the bioreactor may be formed of glass, metal or plastic. Further, the bioreactor may be formed as a reusable bioreactor or as a disposable bioreactor.

The container for accommodating the at least one preparatory fluid may be formed as a mixing container. A mixing container can be utilized to prepare a three-dimensional structure after its printing process with at least one preparatory fluid, like e.g. buffers, media, or other chemicals, prior to seeding cell cultures onto the three-dimensional structure. The mixing container can provide a platform for the removal of debris and/or structural scaffolds during the printing process of structural materials, the equilibration of pH and other factors which can assist in the cell adhesion or growth, the infusion of nutrients and/or media, and/or the addition of chemicals which are required in the processing of the three-dimensional structure. After completing the preparation and processing within the mixing container, the three-dimensional structure can be aseptically transferred utilizing a transfer hatch or aseptic connection to a bioreactor container for the addition of at least one biologically active fluid. Alternatively, the mixing container can be drained and at least one biologically active fluid can be added to the three-dimensional structure through e.g. the dispenser of the printer head. The three-dimensional object can be transferred to an incubator or incubating container for further processing utilizing a transfer hatch any other aseptic connection.

According to another aspect of the present invention, the underlying technical problem has been solved by a sterilizable three-dimensional printer assembly including:
  at least one printing platform;
  at least one printer head for dispensing structural material onto the at least one printing platform in order to form thereon a three-dimensional structure; and
  a moving mechanism for providing a relative displacement between the at least one printer head and the at least one printing platform;
  wherein the moving mechanism comprises at least one curved arm, which is supported by a supporting surface arranged adjacent to the at least one printing platform, where at least one printer head is attached to the curved arm.

Preferably, the moving mechanism comprises at least one curved arm, which is supported by a supporting surface arranged adjacent to the at least one printing platform, wherein at least one printer head is attached to the curved arm.

Any definitions or explanations which have been given with respect to the printer assembly of the sterilizable container as explained above also apply for the printer assembly.

According to another aspect of the present invention, the underlying technical problem has been solved by a method of forming a three-dimensional structure in a container for accommodating at least one of at least one biologically active fluid and at least one preparatory fluid, comprising:
  providing a sterilizable printer assembly in a sterile manner in an area in the container; and
  forming a three-dimensional structure in the container by means of at least one printer head and at least one printing platform of the printer assembly, which are relatively displaced with respect to each other.

Any definitions or explanations which have been given with respect to the sterilizable container apply also for the method, respectively.

Preferably, the step of forming a three-dimensional structure comprises moving at least one curved arm of the printer assembly, which is supported by a supporting surface of the printer assembly adjacent to the at least one printing platform, between a retracted position and an extended position with respect to the supporting surface, wherein at least one printer head is attached to the at least one curved arm for dispensing structural material to the at least one printing platform.

Preferably, the step of forming a three-dimensional structure comprises moving the at least one printer head along the at least one curved arm.

Preferably, the method of forming a three-dimensional structure further comprises the step of opening at least one controlled fluid inlet port in a printer assembly housing, which encloses the printer assembly, for supplying the fluid in the container into the printer assembly housing after the three-dimensional structure has been formed.

Preferably, the method of forming a three-dimensional structure further comprises the step of opening at least one controlled fluid outlet port in the printer assembly housing for allowing a gas exhaust of the printer assembly housing.

These and other objects, features and advantages of the present invention will become more evident by studying the following detailed description of preferred embodiments and the accompanying drawings. Further, it is pointed out that, although embodiments are described separately, single features of these embodiments can be combined for additional embodiments.

BRIEF DESCRIPTION OF THE DRAWINGS

FIG. 2 shows an embodiment of a mixing container containing the three-dimensional printer assembly.

DETAILED DESCRIPTION

Figure 1:
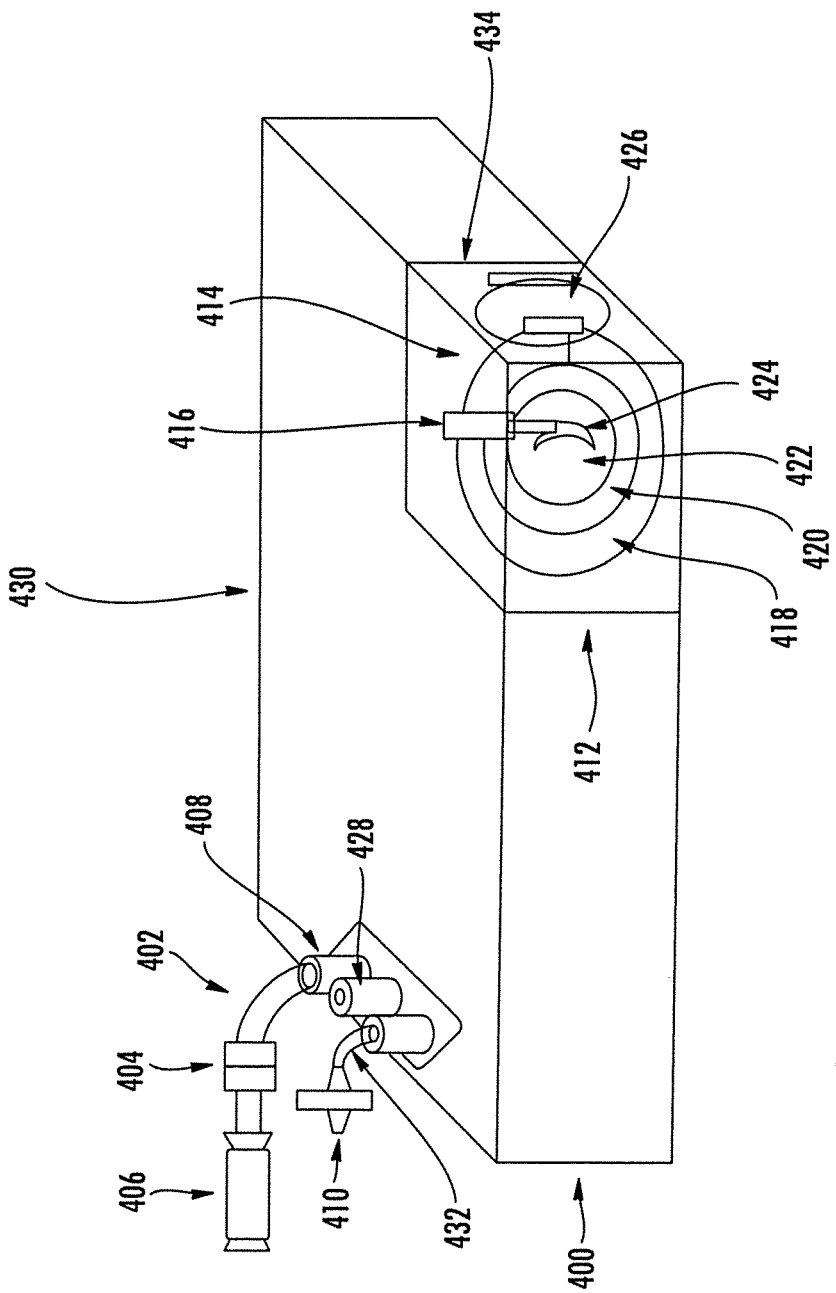
FIG. 1 shows an embodiment of a rocking bioreactor containing a three-dimensional printer assembly.

FIG. 1 discloses an embodiment of a rocking bioreactor 400 (exemplary "container for accommodating at least one biologically active fluid") containing a three-dimensional printer assembly 412 within the interior of a bioreactor container 430. Although only one printer assembly 412 is shown in FIG. 1, it is also possible that a plurality of printer assemblies 412 are provided in the bioreactor container 430.

This embodiment shows a sterilizable bioreactor 400 which can be a flexible walled single-use bag (such as the Cultibag® RM), a rigid walled plastic single-use container, and/or a multi-use glass or stainless steel container. The sterilizable bioreactor 400 may contain a vent filter assembly 410, an inlet fluid assembly 402, and/or an inoculation port 428. The components and assemblies of the sterilizable bioreactor 400 may be sterilized using an approved sterilization method such as by gamma-irradiation, autoclaving, steam-in-place, or chemical sterilant (such as ethylene oxide or vaporized hydrogen peroxide). The entire bioreactor 400 is preferably movable in a rocking motion using an external motorized assembly (not shown) for mixing the contents inside of the bioreactor 400. The bioreactor 400 can utilize baffles, fins, blades or other elements (not shown) to promote and/or restrict mixing within the bioreactor container 430. In particular, the content of the bioreactor 400 are one or more biologically active fluid(s) which are mixed in the bioreactor 400. The biologically active fluids contained within the bioreactor 400 can include but are not limited to tissue culture fluids containing nutrient rich media and cells, suspension cell cultures, adherent cell cultures, suspension cell cultures that are partially adherent, human cell cultures, mammalian cell cultures, insect cell cultures, animal cell cultures, plant cell cultures, yeast cell cultures, eukaryotic cell cultures, bacterial cell cultures, achaebacteria cell cultures, viral cultures, biologically active fluids such as blood, blood serum, blood products, plasma, serum, cerebrospinal fluid, amniotic fluid, lymphatic fluid, intracellular fluid, extracellular fluid, interstitial fluid, transcellular fluid, or other fluids which contain a living biological component, the nutrient rich fluids in support of a biologically active fluid, or a fluid that was processed from a biologically active fluid such as fluid containing proteins, antibodies, lipids, sugars, carbohydrates or other materials.

The vent filter assembly 410 for venting the bioreactor container 430 may be connected with the bioreactor container 430 by means of at least one tubing or with at least one aseptic connector (not shown) and can contain at least one sterilizing and/or non-sterilizing grade vent filter.

The inlet fluid assembly 402 can contain at least one inlet filter 406 which can be a hydrophilic or hydrophobic filter, a depth filter, a pre-filter, a sterilizing grade filter, a mycoplasma retentive filter, a cross-flow (tangential filter), an ultrafiltration filter, a membrane adsorption filter, a virus retentive filter or a combination of filters arranged as a filter train assembly. The purpose of the inlet fluid assembly 402 is preferably to supply sterile media, i.e. the biologically active fluid(s), into the bioreactor container 430.

The inlet fluid assembly 402 can contain at least one aseptic inlet connector assembly 404 which can consist of at least one physical aseptic connector which may comprise two or more components, such as an OPTA® connector with a tubing, or a thermoweldable tubing which can be connected using a Bioweldable® thermoweldable tubing sealer (not shown).

Further, the inlet fluid assembly 402 may comprise an inlet component 408 such as a no-foam inlet, a dip tube, a sparger inlet, or other type of fluid line to the interior of the bioreactor container 430.

Particularly, the sterile media may be supplied to the interior of the bioreactor container 430 via the at least one inlet filter 406, the inlet connector assembly 404 and the inlet component 408. The inlet filter 406 may be connected with the inlet connector assembly 404, and the inlet connector assembly may be connected with the inlet component 408 by means of at least one tubing, respectively. The inlet component 408 allows access to the interior of the bioreactor container 430 for the sterile media.

Additionally, an outlet fluid assembly (not shown) may be provided in the bioreactor container 430 for enabling the media contained in the bioreactor container 430 to escape and/or for enabling a gas exhaust.

The three-dimensional printer assembly 412 contained in the bioreactor container 430 will be explained in detail below.

The three-dimensional printer assembly 412 in the bioreactor container 430 is configured such that three-dimensional structures can be printed inside of the bioreactor container 430 with the majority of sensitive components sealed underneath printer assembly 412. The printer assembly 412 may comprise a printer assembly housing 434, which encloses the printer assembly 412. This provides the possibility that the three-dimensional structure can be printed, while the biologically active fluid is held outside of the printer assembly housing 434 but inside of the bioreactor container 430. In case the printer assembly housing 434 is not provided, the biologically active fluid has to be fed into the bioreactor container 430 after the printing process of the three-dimensional structure 424. The biologically active fluid can be accommodated for this purpose in a standalone bioreactor container beforehand.

A three-dimensional structure 424 may be printed by the printer assembly 412 prior to filling the bioreactor 400 with media or the inoculation of cells through the inoculation port 428. The printed three-dimensional structure 424 may be seeded with cells onto the three-dimensional structure from the bioreactor container 430 over time as the cells proliferate under regulated conditions in the bioreactor container 430. Alternatively, the bioreactor container 430 is already filled with the media and/or the inoculation of cells through the inoculation port 428, while the three-dimensional structure 424 is printed in the printer assembly container 434 of the printer assembly 412.

After the seeding process to the three-dimensional structure 424 and the incubation have been completed, the bioreactor container 430 can be drained and the three-dimensional structure 424 can be removed via a transfer hatch 426 in a wall of the bioreactor container 430 near the three-dimensional printer assembly 412. A sterile transfer bag (not shown) can be connected to the transfer hatch 426, so that the three-dimensional structure 424 can be removed and maintained within a sterile environment. Alternatively, the three-dimensional structure 424 can be removed inside of a biological safety cabinet, isolator or other environmentally controlled container to prevent contamination.

The three-dimensional printer assembly 412 preferably comprises at least one printer head 416 for dispensing structural material onto at least one printing platform in order to form the three-dimensional structure 424. FIG. 1 shows a first printing platform 420 and a second printing platform 422, which are coaxially arranged. The at least one printer head 416 is attached to at least one curved arm 414, which is supported by a supporting surface 418. The supporting surface 418 is arranged adjacent the printing platforms 420, 422 and preferably surrounds the printing platforms 420, 422, as shown in FIG. 1.

Although the embodiment of FIG. 1 has been described with respect to a rocking bioreactor, any disclosure also applies for any other kind of bioreactors. Possible bioreactors are single-use suspension bioreactors, re-usable suspension bioreactors, rocking bioreactors, perfusion bioreactors, agiation bioreactors, photobioreactors, microbioreactors, adherent tissue culture flasks, adherent CellStacks, or external containers connected to bioreactors.

FIG. 2 shows a mixing container 450 containing the three-dimensional printer assembly 412 as explained with respect to the embodiment of FIG. 1. Any explanations regarding the three-dimensional printer assembly 412 given with respect to the embodiment of FIG. 1, therefore, also apply for the embodiment of FIG. 2.

The mixing container 450 may be used alternatively to the bioreactor 400, as disclosed with respect to FIG. 1, as a preferred container for accommodating at least one preparatory fluid.

The mixing container 450 is sterilizable and can be formed of a flexible walled single-use bag (such as a Palletank® mixing bag), a single-use tank liner, a rigid walled plastic single-use container, and/or a multi-use glass or stainless steel container.

The components of the mixing container 450 may be sterilized by using an approved sterilization method such as gamma-irradiation, autoclaving, steam-in-place, or chemical sterilant (such as ethylene oxide or vaporized hydrogen peroxide).

The mixing container 450 may contain a mixing element 456, and the vent filter assembly 410, the inlet fluid assembly 402, and/or the inoculation port 428 as disclosed with respect to FIG. 1. Accordingly, any information which have been given with respect to the vent filter assembly 410, the inlet fluid assembly 402 and the inoculation port 428 with respect to FIG. 1 also apply for the embodiment of FIG. 2, but the bioreactor is replaced by the mixing container 450.

The mixing element 456 may comprise a mixing shaft, an impeller, or fluid mixing device, which are connectable to an external motor (not shown) with a direct connection containing sealed bearings, an extension of the motor shaft into an envelope of the shaft into the mixing container 450, a magnetic coupling (e.g. MagMix®), or a superconducting magnetic coupling (e.g. LevMix®).

Particularly, the mixing element 456 can also contain a plurality of impellers and impeller shapes and designs. Besides, baffles, fins, blades or other elements (not shown) may be used in the mixing container 450 to promote and/or restrict mixing within the mixing container 450.

In FIG. 2, an outlet fluid assembly 468 is shown in a wall of the mixing container 450, which can contain an aseptic connector assembly consisting of a physical aseptic connector which is formed of two or more components, such as an OPTA® connector, or a thermowelding tubing which can be connected by using a Biowelder® thermowelding tubing sealer (not shown). The outlet fluid assembly 468 can contain a filter which can be hydrophilic or hydrophobic filter, a depth filter, a pre-filter, a sterilizing grade filter, a mycoplasma retentive filter, a virus retentive filter, other filter type, or a combination of filters arranged as a filter train assembly. This information regarding the outlet fluid assembly may also apply for the outlet fluid assembly of FIG. 1.

In the mixing container 450, the three-dimensional structure 424 may be printed prior to filling the mixing container 450 with at least one preparatory fluid for preparing the three-dimensional structure 424 for the subsequent seeding process with cell cultures. Alternatively, the preparatory fluids are already present in the mixing container 450 but are prevented from entering the printer assembly housing 434. The biologically active fluids containing the cell cultures may be dispensed by the printer head 416 onto the three-dimensional structure 424 after the preparation process, wherein the biologically active fluids may be pumped from a bioreactor to the mixing container 450. Alternatively, the three-dimensional structure 424 may be transferred in an aseptic manner to a bioreactor. Further alternatively, the prepared three-dimensional structure 424 is transferred to a bioreactor for seeding cell cultures onto the three-dimensional structure 424 in a sterile manner by e.g. a transfer hatch. The preparatory fluids are mixed in the mixing container 450 to ensure uniformity, homogeneity and/or heterogeneity. The three-dimensional structure 424 can be further prepared in the mixing container 450 by the immersion in buffers, media, chemicals (sodium hydroxide and other treatments) detergents (sodium dodecyl sulfate (SDS), Triton-X 100, ionic, non-ionic, zwitterionic and other detergents) enzymes (Trypsin), controlled gases or other fluids from the sterilizable mixing container 450. The printed three-dimensional structure 424 can be aseptically transferred to another container for the final seeding of cells or biological products. After the preparation process of the three-dimensional structure 424 has been completed, the mixing container 450 can be drained via e.g. the outlet fluid assembly 468, and the three-dimensional structure 424 can be removed via a transfer hatch 464 in a wall of the mixing container 450 near the printer assembly 412. A sterile transfer bag (not shown) can be connected to the transfer hatch 464, so that the three-dimensional structure 424 can be removed and maintained within a sterile environment. Alternatively, the three-dimensional structure 424 can be removed inside of a biological safety cabinet, isolator or other environmentally controlled container to prevent contamination.

Alternatively, the preparatory fluids are already contained in the mixing container 450, while the printer assembly 412 prints the three-dimensional structure 424. During that time, the preparatory fluids are outside of the printer assembly housing 434 in the mixing container 450.

In the following, the three-dimensional printer assembly 412, which may be contained in a bioreactor 400 or a mixing container 450 as explained above, will be described in more detail.

FIGS. 3A-3D shows an embodiment of a three-dimensional printer assembly 412 from various perspectives.

Figure 3A:
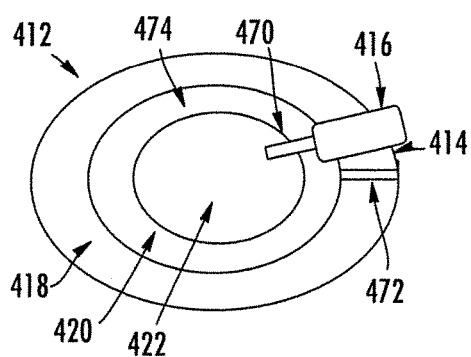
FIGS. 3A-3D show an embodiment of a three-dimensional printer assembly from various perspectives.
Figure 3B:
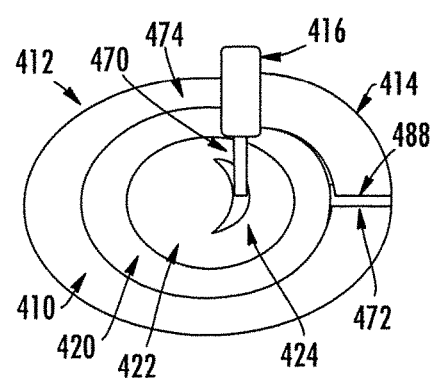

FIGS. 3A and 3B are isometric views of the three-dimensional printer assembly 412 comprising a first printing platform 420 and a second printing platform 422 onto which structural material is dispensed in order to form a three-dimensional structure 424. As shown in FIGS. 3A-3D, the second printing platform 422 is cylindrically shaped and the first printing platform 420 is formed as a ring surrounding the second printing platform 422. In other words, the printing platforms 422 are coaxially arranged. Together, the printing platforms 420, 422 preferably form one printing level. The printing platforms 420, 422 may be fixed or rotatable. The rotation movement may be carried out in a clockwise direction and/or a counter-clockwise direction, preferably at varying speeds.

Alternatively, there is only one printing platform which may be circular or rectangular. Further alternatively, the printing platforms 420, 422 may be rectangular and arranged next to each other in order to form one printing level. Preferably, such rectangular printing platforms are movable along this printing level with respect to each other.

As shown in FIGS. 3A and 3B, the first and second printing platforms 420, 422 are surrounded by a supporting surface 418 forming a supporting platform for a curved arm 414 to which a printer head 416 for dispensing the structural material onto the printing platforms 420, 422 is attached. The cross-sectional shape of the curved arm 414 is preferably identical along its extension.

Figure 3C:
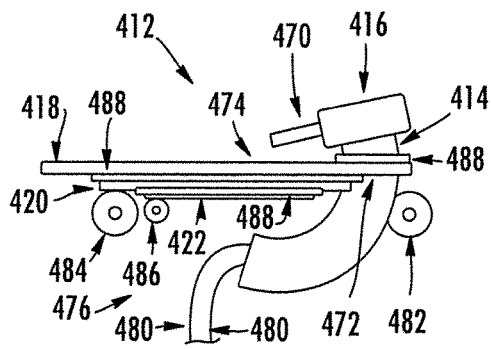
Figure 3D:
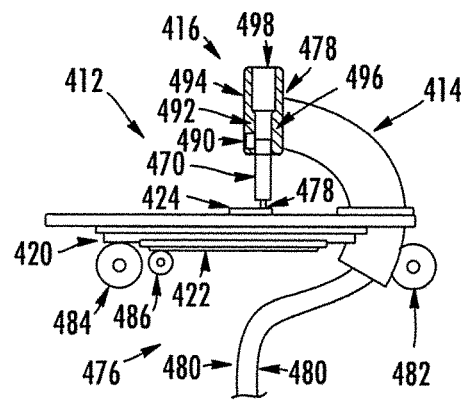

The curved arm 414 is movable between a retracted position, as shown in FIGS. 3A and 3C, and an extended position, as shown in FIGS. 3B and 3D. For this purpose, the supporting surface 418 includes a through hole 472 through which the curved arm 414 extends. Particularly, the through hole 472 has a shape which corresponds to the cross-sectional shape of the curved arm 414 so that the curved arm 414 is movable with respect to the supporting surface 418. In the retracted position, the portion of the curved arm 414 which projects to the upper side 474 of the printer assembly 412 is smaller than the portion of the curved arm 414 projecting to the underside 476 of the printer assembly 412. If the curved arm 414 is in the extended position, the portion of the curved arm 414 projecting to the upper side of the printer assembly 412 is larger than the portion of the curved arm 414 projecting to the underside 476 of the printer assembly 412.

At least one printer head 416 for dispensing structural material onto the printing platforms 420, 422 in order to form a three-dimensional structure 424 is attached to the curved arm 414. Preferably, the printer head 416 is attached to the curved arm 414 at a portion of the curved arm 414 projecting to the upper side 474 of the printer assembly 412, so that the upper side 474 corresponds to the side of the printer assembly 414 where the three-dimensional structure 424 is printed. FIGS. 3A-3D show a printer assembly 412 with only one printer head 416. However, there may be a plurality of printer heads 416, which may have the same functionality or different functionalities.

Although FIGS. 3A-3D show only one printer head 416 attached to the curved arm 414, also a plurality of printer heads 416 can be attached to the curved arm 414. Further, it is pointed out that, although FIGS. 3A-3D shows only one curved arm 414, a printer assembly 412 may also comprise a plurality of curved arms 414.

The printer head 416 may comprise at least one dispenser 470 through which the structural material is dispensable, wherein the dispenser 470 is fixed or movable with respect to the printer head 416. A movement of the dispenser 470 can comprise a pivoting movement or a movement between a retraced position and an extended position of the dispenser 470.

The printer head 416 with the dispenser 470 can be moved into position above the printing platforms 420, 422 by means of a movement of the curved arm 414, which is preferably formed in a rigid manner. Further, the printer head 416 attached to the curved arm 414 may be movable along the curved arm 414 or may be pivotable with respect to the curved arm 414, so that a large dispensing area can be covered by the inventive printer assembly 412. Moreover, the supporting surface 418 may be rotatable.

Further, it is pointed out that the dispenser 470 is not limited to dispensing structural material. It is also possible that the dispenser 470 of the printer head 416 dispenses e.g. biologically active fluid and/or preparatory fluid after the printing process of the three-dimensional structure 424. The biologically active fluid and/or preparatory fluid may be contained in the same bioreactor 400 or mixing container 450 or may be fed in an aseptic manner from another bioreactor or mixing container 450.

FIGS. 3C and 3D show side views of the printer assembly 412.

At least one conduit 480 extends through the curved arm 414 for conducting the structural material 478 from the underside 476 of the printer assembly 412 to the printer head 416. At the underside 476 of the printer assembly 412, a feed assembly (not shown) is provided, which is connected with the at least one conduit 480. The feed assembly may comprise one or more pumps for pumping the structural material 478 towards the printer head 416. Further, the feed assembly may comprise a heating element (not shown) at the underside 476 of the printer assembly 412 by which the structural material 478 is heated up for easier extrusion. Alternatively, a heating element 498 is arranged in the printer head body 494 of the printer head 416 as shown in FIG. 3D.

The embodiment of FIGS. 3A-3D comprises two conduits 480. Through one of these conduits 480 a heating, cooling and/or temperature regulating fluid 496 may circulate. Thereby the temperature of the structural material 478 in the printer head 416 is regulatable. In particular, the temperature regulating fluid 496 may be recirculatable in a closed loop within the conduit 480 and undergo heating, cooling and/or temperature regulation or the temperature regulating fluid 496 can be discarded and new fluid is pumped in as with an open loop pathway. If a conduit 480 is used for dispensing cells, proteins, or other biological/chemical materials that require dispensing at a regulated temperature, the other conduit 480 in which the heating, cooling and/or temperature regulating fluid circulates, may also help to regulate the temperature of the cells, proteins, or other biological/chemical materials.

Preferably, the at least one conduit 480 is formed of a flexible material in order to compensate any movements of the curved arm 414, through which the conduit 480 extends, and/or of the printer head 416 attached to the curved arm 414.

The feed assembly and the conduits 480 may also be used for providing biologically active fluids and/or preparatory fluids to the printer head 416 after the printing process of the three-dimensional structure 424.

Further, a driving assembly is arranged at the underside 476 of the printer assembly by which the at least one curved arm 414 and/or the at least one printing platform and/or the supporting surface 418 are actuatable.

In particular, the driving assembly may comprise at least one arm motor 482, as shown in FIGS. 3C and 3D for moving the curved arm 414 between the retracted position and the expanded position. Preferably, the arm motor 482 comprises one or more rollers and/or gears, which contact the curved arm 414. When the rollers and/or gears are driven by the arm motor 482, the curved arm 414 is shifted towards the desired direction. The rotation direction of the rollers and/or gears define the direction to which the curved arm 414 is moved.

Moreover, the driving assembly may comprise a first printing platform motor 484 for moving the first printing platform 420 and a second printing platform motor 486 for moving the second printing platform 422. The type of the printing platform motor depends on the movement direction of the printing platforms, i.e. whether the printing platforms are rotatable or whether they are shiftable along defined directions. The number of printing platform motors depends on the number of printing platforms which shall be driven by printing platform motors. Provided that printing platforms are rotatable in the same direction, it is also possible that only one printing platform motor drives more than one printing platform.

A further motor may be provided for driving the supporting surface 418, which is not shown in FIGS. 3C and 3D. Besides, a dispenser motor 490 for driving the dispenser 470 in the printer head 416 may be provided. The dispenser motor 490 may be provided at the underside 476 of the printer assembly and may be connected to the dispenser 470 via driving elements extending through the curved arm 414. As shown in view 'D' of FIG. 3 where a cross-sectional view of the printer head 416 is shown, the dispenser motor 490 may be alternatively arranged inside of the printer head body 494 of the printer head 416. The dispenser motor 490 may move the dispenser 470 between the retracted position and the expanded position and/or may drive the dispenser 470 for carrying out pivoting movements. The dispenser motor 490, as shown in FIG. 3D, comprises a flexible linear actuated joint 492 that expands and contracts as the dispenser 470 is moved between the retracted position and the expanded position.

The movable elements of the printer assembly allow a faster and very precise printing process of the three-dimensional structure 424.

The feed assembly as well as the driving assembly are both sensitive elements which should not come into contact with the biologically active fluids and/or preparatory fluids. These assemblies could be damaged when being contacted by the biologically active fluids and/or preparatory fluids, and the materials of the internal components of the assemblies could negatively influence the biologically active fluids and/or preparatory fluids. Additionally, sensors such as temperature sensors, pressure sensors or positional sensors and weighting elements such as load cells, scales or balances can be incorporated into the underside 476 of the printer assembly 412, which also require isolation to prevent damages by biologically active fluids and/or preparatory fluids. Therefore, the feed assembly and the driving assembly are arranged at the underside 476 of the printer assembly 412 and/or components of the feed assembly and driving assembly are located inside of the curved arm 414. In order to seal the upper side 474 of the printer assembly 412, where the at least one biologically active fluid and/or preparatory fluid is present after the three-dimensional structure 424 has been printed, from the underside 476 of the printer assembly 412, various seals 488 may be provided. The seals 488 are arranged such that any leakage of the biologically active fluid(s) and/or preparatory fluid(s) towards the underside 476 of the printer assembly 412 is prevented. Particularly, there may be a seal 488 surrounding the through hole 472 in the supporting surface 418 such that a space between the supporting surface 418 and the curved arm 414 extending through the through hole 472 is sealed.

Further seals 488 may be provided between the respective printing platforms and/or between a printing platform and the surrounding supporting surface 418.

Components of the upper side 474 of the printer assembly 412, like e.g. the printing platforms 420, 422, the curved arm 414 and any components contained in the curved arm 414 and attached to it, may be attachable via a detachable attachment means onto the components of the underside 476 of the printer assembly 412, like e.g. the driving and feed assemblies. Thereby, only parts of the printer assembly 412 can be exchanged if only single components are damaged or components are only constructed for a single use.

The conduit connections can be made with an aseptic or presterilized connection. Alternatively, the materials can be sterilized while being processed such as through heating plastics and metals utilizing a heating element for dispensing or through the sterile filtration of biological active fluids.

Figure 4:
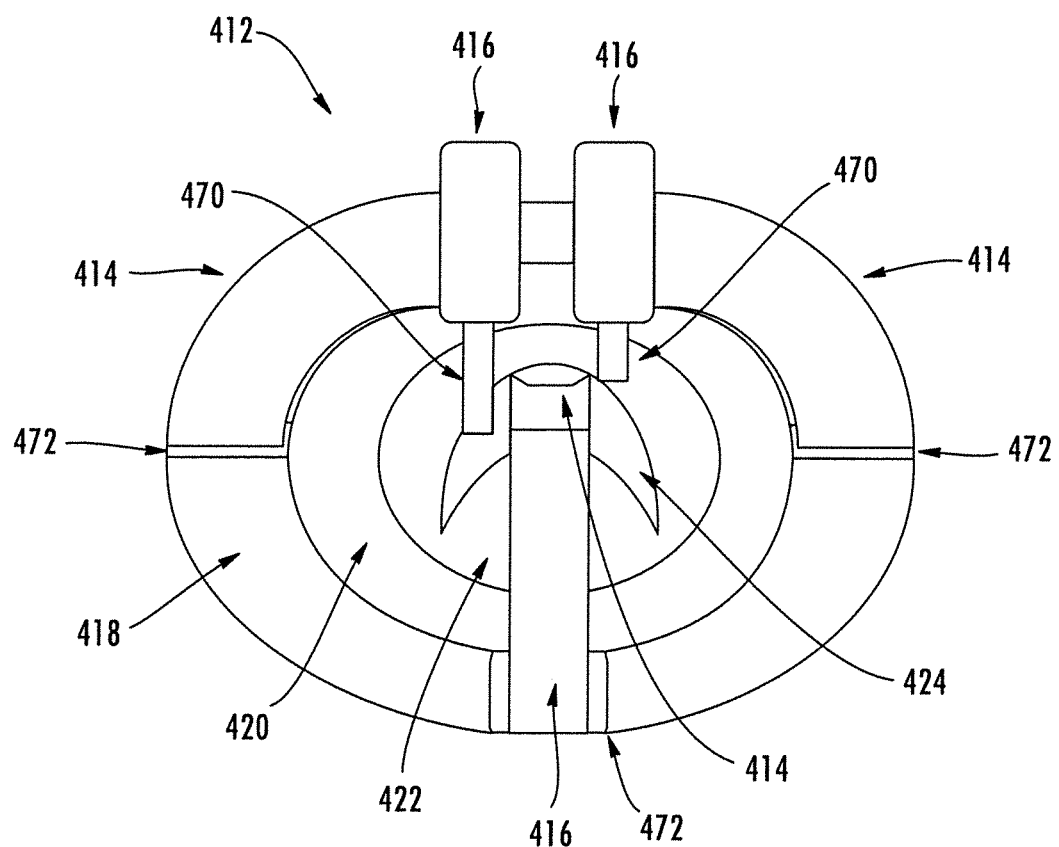
FIG. 4 shows the three-dimensional printer assembly of FIG. 3 with three curved arms.

FIG. 4 discloses the three-dimensional printer assembly 412 of FIG. 3 but with three curved arms 414 and three printer heads 416 attached to a respective curved arm 414. The curved arms 414 are supported by the supporting surface 418 and extend through a respective through hole 472.

The printer heads 416 may have all the same functionality or may have different functionalities as shown in FIG. 4. The printer heads 416 can move independently of one another.

FIGS. 5A-5G shows a process for printing a three-dimensional structure 424 utilizing the three-dimensional printer assembly 412 of FIGS. 3A-3D. Alternatively, also the printer assembly 412 of FIG. 4 could be used.

The printer assembly 412 is located inside of the printer assembly housing 434 which is arranged inside of the bioreactor container 430, which is not shown in FIGS. 5A-5G.

Figure 5A:
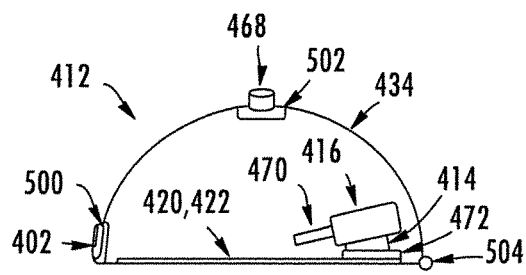
FIGS. 5A-5G shows a process of printing a three-dimensional structure.

FIG. 5A is a side view of the printer assembly 412 inside of the printer assembly housing 434. In this embodiment, the printer assembly 412 features a single printer head 416 with a dispenser 470, which can be moved into position above the at least one printing platform 420, 422 by means of the curved arm 414, which is in the retracted position in FIG. 5A.

The inlet fluid assembly 402 is arranged near the bottom of the printer assembly housing 434 and may comprise at least one controlled inlet valve 500 that opens or seals the inlet fluid assembly 402. The controlled inlet valve 500 can be controlled by an electronic, pneumatic, magnetic and/or mechanical operation, which opens, closes and/or controls the fluid flow into the printer assembly housing 434.

The outlet fluid assembly 468 is arranged at the top of the printer assembly housing 434 and may comprises at least one controlled outlet valve 502 that opens or seals the outlet fluid assembly 468. The controlled outlet valve 502 can be controlled by an electronic, pneumatic, magnetic and/or mechanical operation, which opens, closes and/or controls the fluid flow out of the printer assembly housing 434. The outlet fluid assembly 468 can contain a hydrophobic vent filter, preferably a sterilizing grade hydrophobic vent filter.

The printer assembly housing 434 can be opened to extract the printed three-dimensional structure 424 after it has been completed and properly seeded with cells (provided that the printer assembly is contained in a bioreactor). The printer assembly housing 434 can be opened manually pulling it away from a seal (not shown) and lifting along the direction of a hinged joint 504 at one end of the printer assembly housing 434. In particular, the printer assembly housing 434 may be formed as a hood or may comprises a lid which is openable.

Figure 5B:
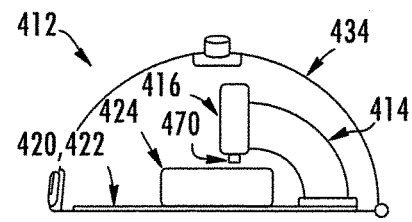

FIG. 5B is a side view of the three-dimensional printer assembly 412 showing the curved arm 414 in the expanded position and the printer head 416 moved towards the free end of the curved arm 414, so that the printer head 416 is positioned above the at least one printing platform 420, 422 and/or the three-dimensional structure 424.

Figure 5C:
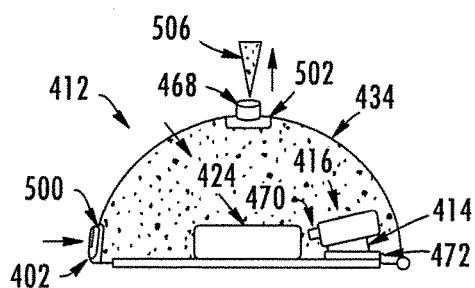
Figure 5D:
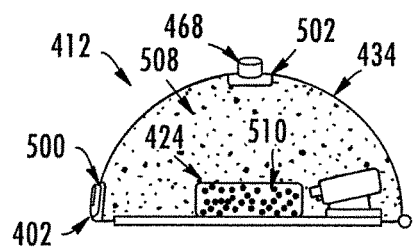

FIG. 5C is a side view of the three-dimensional printer assembly 412 showing a state when the printing process of the three-dimensional structure 424 has been completed. The curved arm 414 has moved back to its retracted position. The controlled inlet valve 500 is opened so that the at least one biologically active fluid is allowed to fill the printer assembly housing 434. The controlled outlet valve 502 is preferably also opened to allow air 506 trapped at the top of the printer assembly housing 434 to vent out and allow the printer assembly housing 434 to be completely filled.

View 'D' of FIG. 5 is a side view of the three-dimensional printer assembly 412 showing a state when the printer assembly housing 434 is filled with the biologically active fluid 508 from the container for accommodating the biologically active fluid. In the present embodiment of FIG. 5, the container for accommodating the biologically active fluid is a bioreactor. Alternatively, a mixing container could be used. In this case, the printer assembly housing 434 would be filled with at least one preparatory fluid. The biologically active fluid, like e.g. cells contained in the biologically active fluid, begins seeding onto the three-dimensional structure 424. Further, the inlet valve 500 of the inlet fluid assembly 402 may be in the open position to allow the biologically active fluid 508 exchange inside the printer assembly housing 434. The biologically fluid 508 can be passively allowed to mix and/or actively mixed by pumping (not shown), spargers (not shown), and/or baffles or fins (not shown) to direct the biologically active fluid movement to provide a proper influx of nutrients, gas exchange and other conditions (temperature, pH, etc.) to maintain healthy cells in the printer assembly housing 434. The mixing elements may be provided in the bioreactor container 430 and/or the printer assembly housing 434. The outlet valve 502 of the outlet fluid assembly 468 is preferably in the closed position after all or the majority of the air is evacuated.

Figure 5E:
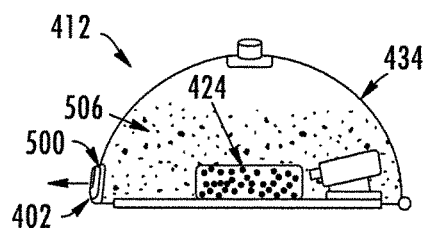

FIG. 5E is a side view of the three-dimensional printer assembly 412, which is filled with gas or air 506 to evacuate the printer assembly housing 434 of all fluid in preparation to extract the seeded three-dimensional structure 424. Gas or air 506 is pumped into the printer assembly housing 434, either through a separate fluid inlet port or through a printer head 416 which contains an air inlet port, to evacuate the biologically active fluid from the printer assembly housing 434. The inlet valve 500 of the inlet fluid assembly 402 is in the open position to allow fluid to flow out of the printer assembly housing 434 as it is displaced by gas or air 506 in the interior of the printer assembly housing 434. Alternatively, bioreactor container 430 is drained and the printer assembly housing 434 empties with fluid as the drained bioreactor container 430 reaches the level of the inlet fluid assembly 402 of the three-dimensional printer assembly 412.

Figure 5F:
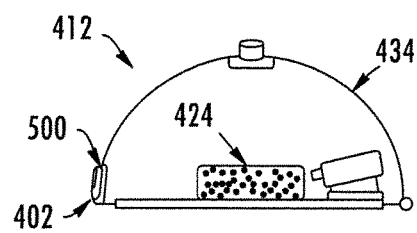

FIG. 5F is a side view of the three-dimensional printer assembly 412 showing a state of the printer assembly housing 434 completely empty of fluid of the bioreactor container 430 and the seeded three-dimensional structure 424 is prepared to be extracted from the printer assembly housing 434. The inlet valve 500 of the inlet fluid assembly 402 is closed to prevent any additional fluid from entering into the printer assembly housing 434 during the extraction procedure. The three-dimensional structure 424 can sit on top of the at least one printing platform or inside of a tray (not shown) with surrounding walls if it requires immersion in fluid during the extraction procedure to prevent fragile cells from dying. Additional preparation steps can take place during this step such as air drying of the three-dimensional structure 424 and/or coating with required material.

Figure 5G:
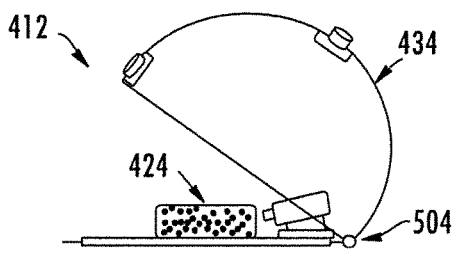

FIG. 5G is a side view of the three-dimensional printer assembly 412 showing a state of the printer assembly housing 434 completely empty of fluid of the bioreactor container 430 and the seeded three-dimensional structure 424 is extracted from the printer assembly housing 434. The printer assembly housing 434 is opened by manually pulling it away from a seal (not shown) and lifting along the direction of the hinged joint 504 at one end of the printer assembly housing 434. The three-dimensional structure 424 can be further placed into a transfer bag (not shown) attached to the bioreactor container 430 via the transfer hatch 426 to maintain sterility. Alternatively, a transfer bag (not shown) could be connected to a transfer hatch (not shown) in the printer assembly housing 434.

It is pointed out that the order of steps disclosed with respect to FIG. 5 refers to a preferred order. It is also possible to omit one or more steps or add one or more steps. The steps can also be repeated in a plurality of cycles such as filling and draining the three-dimensional printer assembly 412 chamber with different biologically active fluids containing different cell types within a sequence to seed multiple cell types or biologically active fluids onto the three-dimensional structure 424.

Any information which has been given regarding the bioreactor 400 and the contained biologically active fluid(s) also apply for the mixing container 450 and the preparatory fluid(s), respectively.

Figure 6:
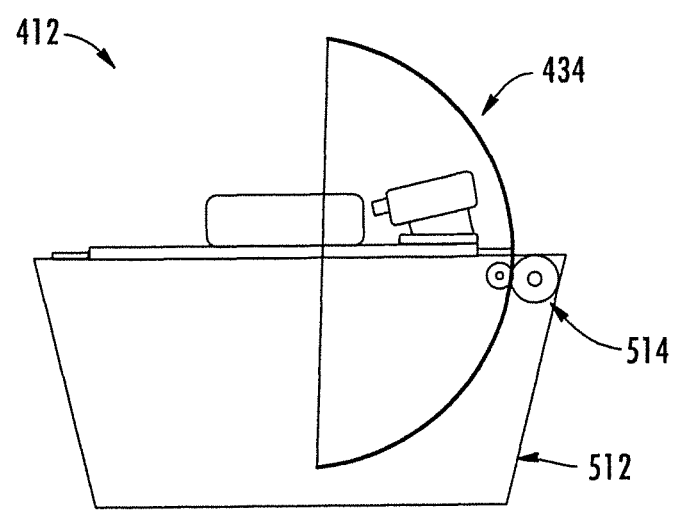
FIG. 6 shows an embodiment of a three-dimensional printer assembly having a storage container.

FIG. 6 shows a side view of the three-dimensional printer assembly 412 as explained with respect to any one of the previously discussed Figures. Additionally, the three-dimensional printer assembly 412 has a storage container 512 underneath the printer assembly 412. When opening the printer assembly housing 434, the printer assembly housing 434 can at least partly enter the storage container 512. The storage container 512 can also collect any fluid which leaks in from the seals of the printer assembly 412. This fluid can be diverted into one or more storage carboys, bags and/or containers using a drainage port, so that the fluid is conducted away from the sensitive components located at the underside 476 of the printer assembly 412.

The storage carboys, bags and/or containers may contain a vent filter and be aseptically connected and/or removed from the printer assembly housing 434.

As shown in FIG. 6, the printer assembly housing 434 comprises a hood. The hood is shifted towards the storage container 512 via a hood motor 514 as an alternative to the hinged joint 504.

Figure 7A:
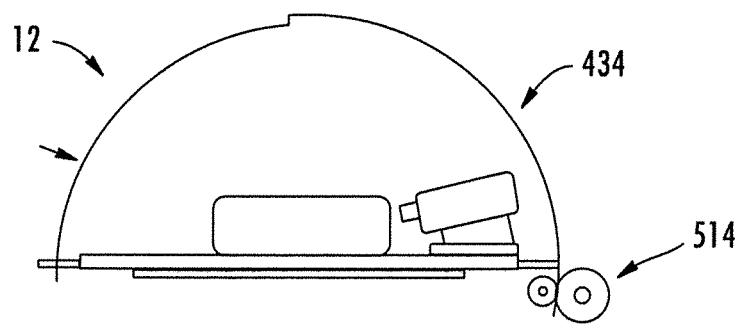
FIGS. 7A and 7B show an embodiment of a three-dimensional printer assembly having a hood in a telescopic manner.
Figure 7B:
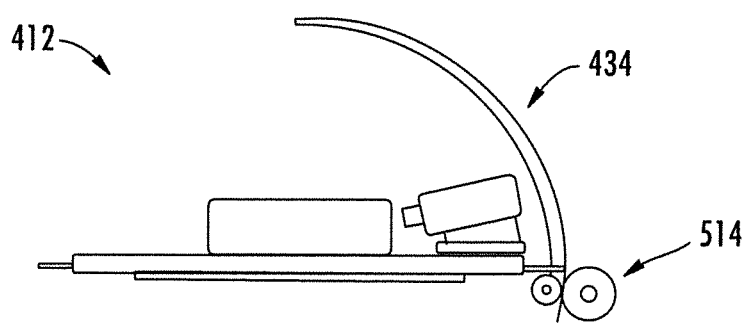

The hood may be formed as a rigid element or may be formed of a plurality of elements which overlap each other in telescope manner when being opened, as shown in FIGS. 7A and 7B. FIG. 7A shows the hood of the printer assembly container 434 in a closed position, and FIG. 7B shows the hood in an opened position, when the elements of the hood overlap each other at least partly. For opening the plurality of elements, the hood motor 514 is preferably provided.

FIGS. 8A-8D show isometric views from the upper side 474 of another embodiment of the three-dimensional printer assembly 412, in which at least one printing platform has a plurality of pores 516. The printer assembly housing 434 is, however, omitted.

Figure 8A:
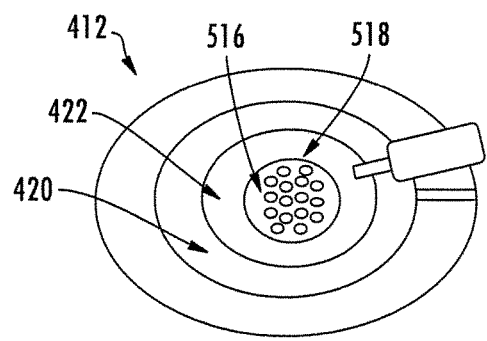
FIGS. 8A-8D show an isometric view of the three-dimensional printer assembly having a plurality of pores in at least one of the printing platforms.

As shown in FIG. 8A, the second printing platform 422 has a plurality of pores 516. The size and shape of the pores 516 and/or the area where the pores 516 are located may vary. Although not shown, it is also possible that the first printing platform 420 provides pores 516. In particular, the pores area 518 where the pores 516 are arranged generally depends on the area where the three-dimensional structure 424 is located. The pores 516 are basically intended to at least partly overlap with the three-dimensional structure 424.

During the printing process of the three-dimensional structure 424 the pores 516 may be in a sealed state.

Figure 8B:
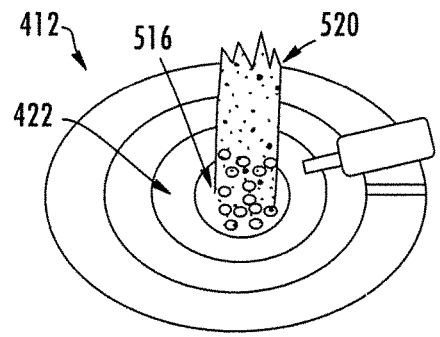

FIG. 8B shows the pores 516 in the open state and allowing compressed gas 520 to flow through them at a regulated pressure and volume. This release of compressed gas 520 through the second printing platform 422 is intended to create internal pathways within the printed three-dimensional structure 424.

Figure 8C:
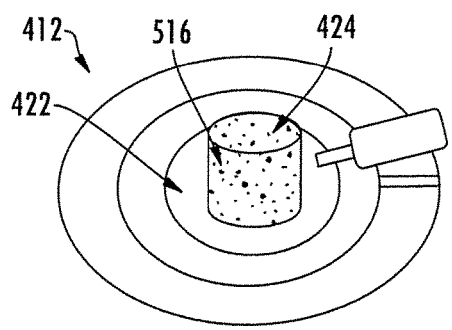

FIG. 8C shows the printing assembly 412, in which the pores 516 are in the closed state during the printing process of the three-dimensional structure 424. In the present case, the three-dimensional structure is made of a soft material or a plurality of soft materials, such as a gel complex or extracellular matrix, which can be pushed away and/or eroded by the force of the compressed gas 520.

Figure 8D:
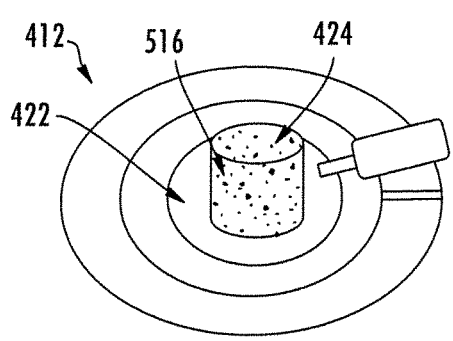

FIG. 8D shows the printing assembly 412 after the compressed gas 520 has flowed through the three-dimensional structure 424. The three-dimensional structure 424 can be held in place during the compressed gas 520 processing using a vacuum seal (not shown) also located on the second printing platform 422. The three-dimensional structure can alternatively and/or additionally be held in place utilizing an attachment mechanism, a holding mechanism, compression on the top of the three-dimensional structure 424, a spike or support into the three-dimensional structure 424, or other mechanism to keep the three-dimensional structure 424 in place during the compressed gas 520 processing.

Channels formed inside of the three-dimensional structure 424 due to the compressed gas 520 processing can be utilized for increasing the surface area for cell adhesion, allowing for fluid, gas and nutrient exchange for these cells, and for creating an internal network for the promotion of cell growth in the interior of the three-dimensional structure 424. The channels' shape, size, frequency, pattern and depth into the three-dimensional structure 424 can be controlled by the regulated compressed gas 520 to provide the optimal seeding and growth for the three-dimensional structure 424.

The compressed gas 520 can alternatively be utilized to pressurize the sealed printer assembly housing 434 and supersaturate the three-dimensional structure 424 with gas. The gas, preferably carbon dioxide or nitrogen, dissolves at high concentrations into the liquid contents of the three-dimensional structure 424, such as gels or softer porous materials. After the three-dimensional structure 424 is supersaturated under pressure with compressed gas 520, the pressure is removed from the printer assembly housing 434 allowing for the dissolved gas in the three-dimensional structure 424 to outgas into the environment and create a network of porous channels to promote cell growth and fluid exchange.

Alternatively or additionally, channels in the three-dimensional structure 424 can be formed by one or more puncturing tools which extend through the pores 516. When the pores 516 are in the opened state, the puncturing tools rise through them at a regulated force and height. The puncturing tools can be of a fixed size and shape, can telescope from a shorter length to a longer length, can feature subtool shapes that retract out of the main puncturing tool, and/or contain channels where compressed gas and/or fluid can pass through.

A straight puncturing tool can be tube, shaft, or needle which can create a channel in the three-dimensional structure 424, remove a portion of the three-dimensional structure 424 in the internal volume of the tube, or vacuum out a portion of the three-dimensional structure 424. A flexible puncturing tool can be flexible, bending under strain and can create non-linear channels inside of the three-dimensional structure 424. A puncturing tool with a bend can provide wider channels inside of the three-dimensional structure 424. A rectangular puncturing tool can be used to push a portion of the three-dimensional structure 424 out of the other end of the three-dimensional structure 424 to create a complete flow path through. A straight edge knife puncturing tool can be a blade which slices through the three-dimensional structure 424 creating a channel. A compressed gas/fluid puncturing tool can puncture into the surface of the three-dimensional structure 424 and expand a channel through compressed gas and/or by fluid medium which dissolves or erodes the interior of the three-dimensional structure 424 to create a channel pattern. A puncturing tool with a balloon catheter can create a cavity and/or void within the three-dimensional structure 424 by the expansion of a balloon under compressed gas or fluid pressure. The puncturing tool with a balloon catheter can additionally employ a stent to keep a channel pathway opened after the balloon has been deflated and the puncturing tool has been removed. A puncturing tool with a plurality of balloon catheters can create a cavity and/or void within the three-dimensional structure 424 in a variety of shapes and patterns. A puncturing tool with secondary subtool protrusions can have a plurality of secondary shapes, patterns, and designs come out of the primary puncturing tool after insertion into the three-dimensional structure 424. The secondary subtool protrusions can be of a fixed size and shape, can telescope form a shorter length to a longer length, and can contain internal channels where compressed gas and/or fluid can pass through. A puncturing tool with multi-step subtool protrusions can have a plurality of secondary, tertiary, and so on shapes, patterns, and designs coming out of the primary puncturing tool after insertion into the three-dimensional structure 424.

Further alternatively or additionally, one or more holders may be arranged on the supporting surface 418 of the printer assembly 412. A surface of the holder facing the three-dimensional structure 424 comprises a plurality of pores 516 through which the compressed gas 520 flows and/or a plurality of puncturing tools are utilized in order to form channels in the three-dimensional structure 424. The size and shape of the pores 516 may vary. The pores 516 can be in a sealed state or can remain open during the printing process of the three-dimensional structure 424.

FIGS. 9A-9D shows another embodiment of the printer assembly 412 having a membrane dispenser 522.

Figure 9A:
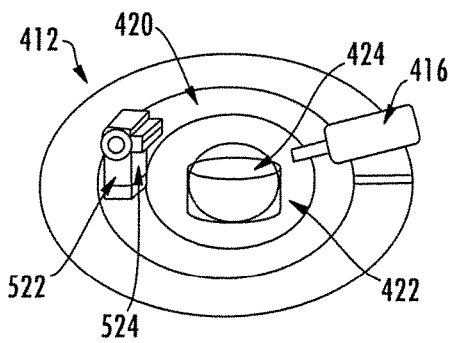
FIGS. 9A-9D show an isometric view of the three-dimensional printer assembly having a membrane dispenser.

FIG. 9A shows the printer assembly 412 as e.g. described with respect to FIGS. 3A-3D. At least one membrane dispenser 522 is arranged on the first printing platform 420, as shown in FIG. 9, or on the supporting surface 418. The membrane dispenser 522 preferably has a membrane cutter 524 for cutting the membrane.

FIG. 9A shows a state when a three-dimensional structure 424 has been printed by the printer head 416.

Figure 9B:
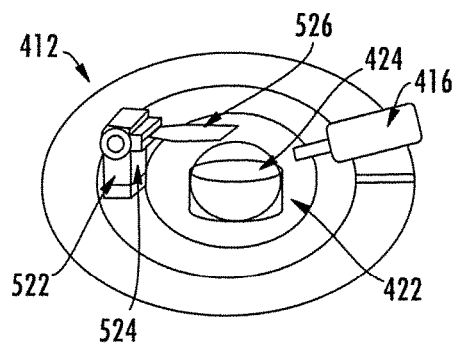

FIG. 9B shows state, when the membrane dispenser 522 dispenses a first membrane 526 into a defined position above the three-dimensional structure 424.

Figure 9C:
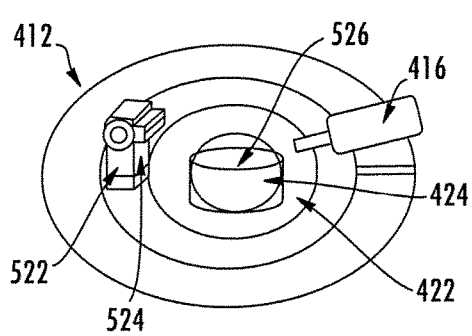

FIG. 9C shows a state, when the membrane cutter 524 cuts the first membrane 526 off when it is dispensed into position above the three-dimensional structure 424 and the first membrane 526 becomes part of the three-dimensional structure 424.

Figure 9D:
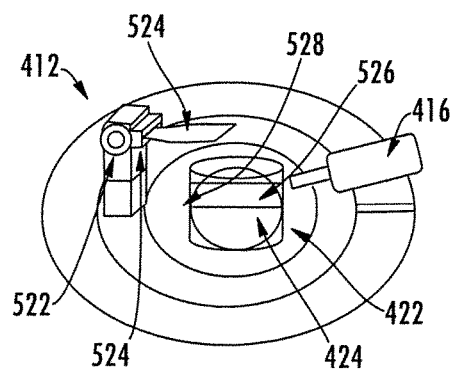

FIG. 9D shows a state, when a second portion 528 of the three-dimensional structure 424 is printed onto the first membrane 526. The membrane dispenser 522 dispenses a second membrane 530 into a defined position above the second portion 528 of the three-dimensional structure 424 prior to being cut by the membrane cutter 524.

The number of layers in a three-dimensional structure are not limited to a specific number. FIGS. 9a-9D shows only the exemplary number of two membrane layers.

Alternatively or additionally to membranes, the membrane dispenser 522 may dispense one or more fleeces, sponges and/or thin films. Any of the dispensed materials may be hydrophilic and/or hydrophobic and can be composed of a fast dissolving material, such as a hydrophilic polymer, a slow dissolving material such as cellulose which can be absorbed into the structure over time, or a non-dissolvable material such as polypropylene fleece or polyethersulfone membranes. These materials are intended to create internal pathways and scaffolding within the three-dimensional structure 424 for cells, fluids, gas and nutrient exchange to take place. These materials can additionally comprise nutrient based materials which are absorbed over time by the three-dimensional object growing on the three-dimensional structure 424. Complete membranes, fleece layers, sponges, and thin films can be utilized or only small bits of each of these structures can be mixed into the three-dimensional structure 424.

Further alternatively or additionally, the membrane dispenser 522 may dispense Shape Memory Polymers (SMPs), Shape Memory Alloys, and/or Cold Hibernated Elastic Memory (CHEM) Foams. Those materials can alter their shape, size, and/or position based on an external factor such as temperature, pH, light, electricity or other factors. The materials can be sprayed onto the three-dimensional structure 424, printed directly onto the three-dimensional structure 424, dispensed with a backing onto the three-dimensional structure 424, or mixed in with another material deposited onto the three-dimensional structure 424.

Preferably, the method of forming a three-dimensional structure 424 further comprises the step of printing dense material into the three-dimensional structure 424 to prevent the three-dimensional structure 424 from floating within the bioreactor container 430 or mixing container 450 once it is filled with fluid.

The dense material can comprise weights, low melting point metals, or other materials heavier than fluid materials to prevent the three-dimensional structure 424 from moving during the fluid filling or mixing/agitation steps. The printing of dense material can occur on the initial base structure printed onto the printing platform(s) which can serve as an anchor to the three-dimensional structure 424 printed on top of the base structure. At the conclusion of the printing process and during the removal of the three-dimensional structure 424 from the bioreactor container 430 or the mixing container 450, this initially structurally weighted base can be separated and removed from the desired portion of the three-dimensional structure 424.

Preferably, the method of forming a three-dimensional structure 424 further comprises the step of an attachment or holding mechanism to secure the three-dimensional structure 424 to the at least one printing platform 420, 422 and prevent it from moving during the fluid filling or mixing/agitation steps. The attachment or holding mechanism can comprise a clamp, cover, or holder that completely or partially covers the three-dimensional structure 424 after the printing has completed and prior to fluid filling the bioreactor container 430 or mixing container 450. The clamp can consist of a plurality of flat panels, beams, or rods which are positioned on the three-dimensional structure 424 on top or on the sides. The holder can additionally consist of an L-style, T-style, S-style, C-style or other style brace on the at least one printing platform 420, 422 which can extend, hinge, or swivel into place to completely or partially cover the three-dimensional structure 424. The clamp can alternatively by provided by at least one printer head 416 in the extended position which can touch the top of the three-dimensional structure 424 and hold it in place on the at least one printing platform 420, 422. The three-dimensional structure 424 can be designed to incorporate flat surfaces to make it easier for a holding mechanism to clamp or hold onto. A moving panel from the top of the printer assembly 412 can be moved into position after printing process has completed to hold the top of the three-dimensional structure 424 and apply pressure to secure it to the printing platform 420, 422. Alternatively a vacuum source from the printing platform 420, 422 can provide suction to secure the three-dimensional structure 424 to the printing platform 420, 422.

In an alternate embodiment the adherence of melted material such as plastic (PLA, ABS, Polypropylene, etc.) or melted metals which are extruded from the printer heads 416 onto the printing platform 420, 422 can form a secure bond. This property can be exploited by modifying the surface of the printing platform 420, 422 with grooves, ripples, bumps, or other structures that increase the surface area and promote the securing of the extruded materials thus preventing the movement of the three-dimensional structure 424. In addition a single or plurality of structures on the printing platform 420, 422, such as a cone or other structure with a head wider than the base, a hook, a spike, a tree, or other structures that can either be printed on top of extruded material during the printing process or deployed into the three-dimensional structure 424 after the printing process has been completed. In both instances a base of extruded material can secure the three-dimensional structure 424 to the printing platform 420, 422. At the conclusion of the printing process and during the removal of the three-dimensional structure 424 from the bioreactor container 430 or mixing container 450 this initial base layer secured to the printing platform 420, 422 can be separated and removed from the desired portion of the three-dimensional structure 424.

Preferably, the method of forming a three-dimensional structure 424 further comprises the step of tethering the three-dimensional structure 424 to the at least one printing platform 420, 422. The three-dimensional structure 424 can be secured using rope, cords, bands, chains, or other securing strands to hold the three-dimensional structure 424 in place on the printing platform 420, 422. Alternatively, the securing strands can be utilized to tether the three-dimensional structure 424 to the printing platform 420, 422 to allow it to float within the bioreactor container 430 or mixing container 450 to maximize the surface area exposed to the biologically active fluid and/or preparatory fluid without having it moved too far from the printing platform 420, 422 or be damaged by an active agitation or mixing mechanism. The securing strands can be available on the printing platform 420, 422 and printed into the three dimensional structure 424, they can be printed by the three-dimensional printer assembly 412 to a securing mechanism such as a hoop or loop, or they can be added after the printing process by an alternative mechanical mechanism. The length of the tethering can be determined by the purpose and requirements of the three-dimensional structure 424.

The floating of the three-dimensional structure 424 can be promoted by printing with materials of low density, in particular those with a lower density than the fluid filling the bioreactor container 430 or mixing container 450, by the addition of external structures such as cork or foam, gas filled balloons, bladders or other structures, or the printing of voids or other buoyant structures within the three-dimensional structure 424 and filling it with a gas or fluid that is less dense than the fluid filled in the bioreactor container 430 or mixing container 450.

Preferably, the method of forming a three-dimensional structure 424 further comprises the step of dispensing structural, preparatory and/or biologically active fluids while the three-dimensional structure 424 is partially or completely submerged in the fluid contained in the bioreactor container 430 or the mixing container 450. The printer heads 416 can actively dispense or pump the respective fluid into the printer assembly 412 onto the three-dimensional structure 424 while the structure 424 is submerged. The printer head 416 can preferentially dispense fluids which are denser than the filling fluid such as gels or dense particulates which can coat the three-dimensional structure 424. These gels and particulates can carry nutrient rich materials which can assist with the adhesion and promote preferential cell growth onto sections or the entire three-dimensional structure 424. Additionally, the printer heads 416 can dispense materials that are mixed into solution such as lighter particulates, chemicals to regulate pH or other measured conditions, or biologically active fluids. Additionally or alternatively compressed air or compressed gases from a printer head 416 can be injected into the three-dimensional structure 424 or the printer assembly housing 434 itself.

Preferably, the method of forming a three-dimensional structure 424 further comprises the step of dispensing materials into a defined position utilizing a dispensing assembly located on the at least one printing platform 420, 422 which can dispense materials from the driving assembly. The dispensing assembly can be fixed to the printing platform 420, 422 in either stationary position or can move with the positioning or rotation of one or more of the printing platforms 420, 422. The dispensing assembly structure located within the printer assembly 412 can extend, articulate, bend, or rotate into position above the three-dimensional structure 424 for properly positioning the dispensed materials which can include but are not limited to membranes, fleeces, sponges, thin films, or shape memory polymers. These materials are added to the three-dimensional structure 424 to promote cell growth and adhesion by increasing the availability, circulation, and exchange of nutrients, gases, and the removal of waste products allowing for the support cell populations internal to the three-dimensional structure 424. The dispensed materials can be cut by a cutting assembly located on the dispensing assembly. The internals of the dispensing assembly can connect to the driving assembly where the materials can be fed through a conduit connection and driven by a motor mechanism such as with the spooling of printer paper. The materials placed within the driving assembly can be pre-sterilized utilizing an approved sterilization method which can be separate from the method utilized for either the container assembly, the printing assembly, or the driving assembly. An aseptic connection can be made to transport the materials from the driving assembly to the feed assembly of the dispensing assembly.

Preferably, the method of forming a three-dimensional structure 424 further comprises the step of dispensing electronic materials into a defined position utilizing a dispensing assembly located on the at least one printing platform 420, 422 which can dispense materials from the driving assembly. This assembly can dispense electronic components and materials in much the same way as it can dispense membranes and fleeces. The electronic materials to be dispensed into the three-dimensional structure 424 can include but are not limited to sensors, circuit boards, processors, batteries, displays, network or communication devices, or other electronic devices. The internals of the electronic materials dispensing assembly can connect to the driving assembly where the materials can be fed through a conduit connection and driven by a motor mechanism. The difference here is that electronic components are sensitive to some sterilization methods such as gamma irradiation or heat treatment. The electronic materials placed within the driving assembly can be pre-sterilized utilizing an approved sterilization method such as chemical sterilization which can be separate from the method utilized for either the container assembly, the printing assembly, or the driving assembly. An aseptic connection can be made to transport the materials from the driving assembly to the feed assembly of the dispensing assembly.

Preferably, the printer assembly housing 434 comprises of at least one positional sensor for the auto-calibration of the printer head 416 with respect to the printing platform 420, 422. Due to the enclosure around the printer assembly and that it was pre-sterilized by an approved sterilization method it would be difficult to manually calibrate the positions of the printer head 416 relative to the printing platform 420, 422 to ensure an accurate printing of a three-dimensional structure 424. Therefore, an automated calibration of the printer head 416 with respect to the printing platform 420, 422 is preferred. Methods for utilizing a laser or light positioning off a reflective material or the positioning of a target with a camera array is described in 'Single-Use Biological 3 Dimensional Printer' disclosed in US 20150035206A1. The method described here is the utilization of a plurality of positional sensors within, on top of, or directly underneath the printing platform 420, 422. These positional sensors can consist of RFID tags, NFC Tags, electronic stripes, magnets, or other positional tags which can provide a sensing device with positional information. The sensors can additionally or alternatively be visual markers such as augmented reality markers or targets. These sensors can be single-use and disposed of along with the assembly or multi-use in the case of sensors underneath the printing platform 420, 422. The detection device can be preferentially located within the printer head 416 which can be extended and moved to reach all of the positions on the printing platform 420, 422. In the embodiment of the visual markers the detection device can be a camera device, preferentially a video camera device which can determine the position and angle of a marker or target of known size. This can be utilized to automatically calibrate the positioning of the printer head 416 to the printing platform 420, 422 prior to printing, in the middle of printing, or at the conclusion of the printing process.

Preferably, the printer assembly 412 comprises of at least one visual sensing device for the detection of a visual marker, target, or positional tag on the printing platform 420, 422. The camera, preferentially a video camera, is preferentially located on the printer head 416. The camera preferably contains adjustable lenses which can autofocus on the visual marker at different distances between the printing platform 420, 422 and the printer head 416. The camera can contain a light, such as an LED light, to observe the printing platform 420, 422 in a dark enclosure, such as within a bag holder or stainless steel bioreactor body. The camera can additionally be utilized for determining the accuracy of the printing of the three-dimensional structure 424 and can stop the printing process if the structure is defective or if the auto-calibration was incorrect. A macro and/or a microscopic lens can be incorporated to determine the details and quality of the printing of the structure and/or to visualize the growth of cells on the three-dimensional structure 424. The camera containing a light can image the three-dimensional structure 424 after the structure is submerged in a fluid. The camera can additionally or alternatively be utilized to determine the color of a chromic dye within the fluid media as an indicator for pH or other measureable value or to determine if a contamination is present within the chamber as described in 'Assembling Method, Operating Method, Augmented Reality System and Computer Program Product' U.S. Pat. No. 8,982,156 B2.

Preferably, the printer assembly 412 comprises of at least one sensing device located on the printing platform 420, 422 and/or the printer head 416 for the detection of a measureable variable. These sensors can consist of temperature sensors, Resistance Temperature Detectors (RTDs), pH sensors, dissolved oxygen sensors, or other sensor types that provide information about the interior of the printer assembly 412 and/or of the container 430, 450. The sensors can be single-use components within either the printer assembly 412 or the driving assembly or multi-use components within the driving assembly protected from the biologically active fluid in the container enclosure. The sensors can transfer the data from wired or wireless connections. The wired cables from the sensors can transfer data through cables positioned through the conduit linking the printer assembly 412, printer heads 416, and printing platform 420, 422 to the driving assembly. The data from the sensors can be connected to the printer assembly 412, the container controlling unit, an external wireless device, an internal network, or an external cloud network.

Preferably, the printer assembly 412 comprises of at least one load cell and/or a weighing device located on the printing platform 420, 422 for the detection of the weight of the three-dimensional structure 424 during the printing process. The load cell and/or weight sensor can determine the accuracy of the printed structure 424 during the printing process based on the amount of material deposited from the printer head 416. The load cell and/or weight sensor can also determine the weight of the three-dimensional structure 424 prior to the addition of a biologically active fluid and the weight of the structure 424 after the biological material or cells have deposited on the structure 424 after the fluid has been removed from the container 430. The printing assembly enclosure can be drained at a regular temporary interval to determine the rate and trending of biological growth on the three-dimensional structure 424 based on the measurements of increasing weights from the load cell and/or weight sensor.

Preferably, the container 430, 450 comprises at least one load cell and/or a weighing device located external to the container 430, 450. The load cell and/or weight sensor can determine the weight of the biologically active fluid and/or preparatory fluid added to the container 430, 450 as well as a measurement of the printed three-dimensional structure 424 during the printing process. The load cell and/or weight sensor can determine the weight of the biologically active fluid and/or preparatory fluid added to the container 430, 450 to regulate the proper volume of filling. The load cell and/or weight sensor can also determine the weight of the three-dimensional structure 424 prior to the addition of a biologically active fluid and/or preparatory fluid and the weight of the structure 424 after the material or cells have deposited on the structure after the fluid has been removed from the container 430, 450. The printer assembly housing 434 can be drained at a regular temporary interval to determine the rate and trending of biological growth on the three-dimensional structure 424 based on the external weight measurements of the entire container.

Preferably, the printer assembly 412 comprises of at least one dispenser 470 in the printer head 416 which can articulate in at least one direction. The dispenser 470 can articulate, bend, or move in at least one direction to provide an additional degree of freedom for the printing process of the three-dimensional structure 424. The dispenser 470 can pivot along a single plane or it can swivel on a ball joint to articulate within a plurality of planes. The dispenser barrel can be moved up or down along a vertical axis to extend or contract the length and the distance to the printing platform 420, 422 and/or the three-dimensional structure 424. The print head barrel can move within the vertical axis by utilizing a linear actuator, a track, or a screw. In the embodiment of a screw the length of the print head barrel can be extended or retracted based on the auger motion of the screw. The combined movements of the curved arm 414, the printer head 416, the printing platform 420, 422, and the dispenser 470, the described printer assembly 412 can perform a multi-axis print of a three-dimensional structure 424.

Preferably, the container comprises a transfer hatch where a three-dimensional structure 424 can be aseptically removed from the printer assembly 412 or an external component can be aseptically inserted into the container and placed onto the printing platform 420, 422. The transfer hatch can connect to a sterile transfer bag where the three-dimensional structure 424 or external component can be placed when moving it either into or out of the printer assembly 412. The operator can grasp the external portion of the transfer bag and invert it to grasp the object and move it from the container into the transfer bag or from the transfer bag to the container. In other embodiments the transfer bag can contain a gloved element where the operator can place their hand into to gently transfer the object. In an alternate embodiment the operator can utilize a grabber manipulator tool which is integrated into the transfer bag. The transfer bag can be sterilized by gamma irradiation, autoclaving, a chemical sterilant or other validated sterilization procedure. The transfer hatch can alternatively be connected to an isolator or glove box for transferring objects into or out of the printing assembly and/or the container.

It is pointed out that, although the present invention has been described with respect to various embodiments, these embodiments can be combined.

LIST OF REFERENCE NUMERALS

400 bioreactor
402 inlet fluid assembly
404 inlet connector assembly
406 inlet filter
408 inlet component
410 vent filter assembly
412 three-dimensional printer assembly
414 curved arm
416 printer head
420 first printing platform
418 supporting surface
422 second printing platform
424 three-dimensional structure 426 transfer hatch
428 inoculation port
430 bioreactor container
432 vent tubing
434 printer assembly housing
450 mixing container
456 mixing element
464 transfer hatch
468 outlet fluid assembly
470 dispenser
472 through hole
474 upper side of the printer assembly
476 underside of the printer assembly
478 structural material
480 conduit
482 arm motor
484 first printing platform motor
486 second printing platform motor
488 seal
490 dispenser motor
492 actuated joint
494 printer head body
496 temperature regulating fluid
498 heating element
500 inlet valve
502 outlet valve
504 hinged joint
506 air
508 biologically active fluid
510 cell
512 storage container
514 hood motor
516 pore
518 pores area
520 compressed gas
522 membrane dispenser
524 membrane cutter
526 first membrane
528 second portion of the three-dimensional structure
530 second membrane

What is claimed is:

1. A sterilizable container for exposing a sterile three-dimensional structure to at least one of at least one biologically active fluid and at least one preparatory fluid, comprising:
a sterilizable printer assembly housing that occupies a first area within the container;
a sterilizable three-dimensional printer assembly disposed in the printer assembly housing and including:
at least one printing platform,
at least one printer head for dispensing structural material onto the at least one printing platform in order to form thereon a three-dimensional structure, and
a moving mechanism for providing a relative displacement between the at least one printer head and the at least one printing platform;
a second area in the container configured to contain at least one of the biologically active fluid and the preparatory fluid in a sterile state and isolated from the first area of the container; and
a selectively openable passage between the first and second areas of the container, such that the fluid can reach the three-dimensional structure formed by the printer assembly in the first area of the container.

2. The container of claim 1, wherein the moving mechanism comprises at least one curved arm that is supported by a supporting surface arranged adjacent to the at least one printing platform, wherein at least one printer head is attached to the curved arm.

3. The container of claim 2, wherein the curved arm is movable between a retracted position and an extended position with respect to the supporting surface.

4. The container of claim 3, wherein the curved arm extends through a through hole in the supporting surface.

5. The container of claim 2, wherein the at least one printer head is at least one of movable along the curved arm and pivotable with respect to the curved arm.

6. The container of claim 1, wherein the printer head has at least one dispenser for dispensing the structural material onto the at least one printing platform, wherein the dispenser is fixed or movable with respect to the printer head.

7. The container of claim 2, wherein the supporting surface is movable or stationary.

8. The container of claim 2, further comprising a driving assembly arranged at an underside of the printer assembly for actuating at least one of the at least one curved arm and the at least one printing platform and the supporting surface, wherein the underside of the printer assembly is sealed with respect to an upper side of the printer assembly where the three-dimensional structure is formed by the printer assembly.

9. The container of claim 8, further comprising a feed assembly arranged at the underside of the printer assembly and connected to the at least one printer head via at least one conduit extending through the at least one curved arm for feeding the at least one printer head with the structural material for forming the three-dimensional structure in the first area of the container.

10. The container of claim 1, wherein the printer assembly housing comprises at least one of at least one controlled fluid inlet port and at least one controlled fluid outlet port for allowing a fluid exchange between the printer assembly housing and the second area of the container.

11. The container of claim 1, wherein the printer assembly housing is openable.

12. The container of claim 1, wherein the container is one of a bioreactor and a mixing container.

* * * * *